United States Patent [19]

Arlinghaus et al.

[11] Patent Number: 5,780,232

[45] Date of Patent: Jul. 14, 1998

[54] DNA SEQUENCING, MAPPING, AND DIAGNOSTIC PROCESSES USING HYBRIDIZATION AND STABLE ISOTOPE LABELS OF DNA

[75] Inventors: Heinrich F. Arlinghaus; K. Bruce Jacobson, both of Oak Ridge, Tenn.

[73] Assignee: Atom Sciences, Inc., Oak Ridge, Tenn.

[21] Appl. No.: 654,181

[22] Filed: May 28, 1996

[51] Int. Cl.$^6$ ..................... C12Q 1/68
[52] U.S. Cl. ............. 435/6; 435/810; 422/68.1; 422/69; 422/78; 422/80; 422/82.05; 422/82.09; 436/501; 536/25.3; 935/77; 935/78; 935/86; 935/87
[58] Field of Search ............... 435/6, 69.1, 810; 436/501; 536/22.1, 23.1, 24.1, 24.3-33, 25.3; 935/77, 78, 86, 87; 422/68.1, 69, 78, 80, 82.05, 82.09

[56] References Cited

U.S. PATENT DOCUMENTS

| | | | |
|---|---|---|---|
| 5,064,754 | 11/1991 | Mills ........................ | 435/6 |
| 5,202,231 | 4/1993 | Drmanac et al. ............. | 435/6 |
| 5,547,835 | 8/1996 | Koster ....................... | 435/6 |

FOREIGN PATENT DOCUMENTS 89460  11/1989  WIPO.

*Primary Examiner*—Ardin H. Marschel
*Attorney, Agent, or Firm*—Pitts & Brittian, P.C.

[57] ABSTRACT

A DNA sequencing, mapping, and diagnostic process which includes the steps of labeling nucleotide segments or peptide nucleic acids (PNAs) with one or more atoms of specific stable or long-lived radioactive isotopes of a selected element that do not normally occur in DNAs, ODNs or PNAs such that the nucleotide segment or PNA has specific stable or long-lived radioactive isotope of a specified selected element at a terminal or an interior position; hybridizing the labeled nucleotide segment or PNA to complementary nucleic acid segments or PNAs which are fixed on a hybridization surface; and, using mass spectrometric techniques, including RIS, to analyze the presence and position of the labeled hybridized nucleotide segments or PNAs which are bound to the fixed nucleotide segments or PNAs.

67 Claims, 3 Drawing Sheets

$^{118}Sn/^{120}Sn$ Isotope Ratio 1.4+
1.2 to 1.4
1.0 to 1.2
0.8 to 1.0
0.6 to 0.8
0.4 to 0.6
0.2 to 0.4
0.0 to 0.2

← 6.2 mm →

DNA SEQUENCING, MAPPING, AND DIAGNOSTIC PROCESSES USING HYBRIDIZATION AND STABLE ISOTOPE LABELS OF DNA

TECHNICAL FIELD

This invention relates to the fields of DNA sequencing and diagnostics. More particularly, this invention relates to processes of DNA sequencing, mapping and diagnostics utilizing stable or long-lived radioactive isotopes, rather than short-lived isotopes or fluorescent substances, to label short segments of DNA commonly known as oligodeoxynucleotides (ODNs).

BACKGROUND ART

The nuclei of living cells possess chromosomes which contain the genetic information necessary for the growth, regeneration and other functioning of organisms. Instructions concerning such functioning are contained in the molecules of deoxyribonucleic acid (DNA). DNA is contained within the chromosome in a form of complimentary strands commonly thought of as being configured in a double helix.

Genetic information in DNA is known to be contained within the sequence of nucleotide bases which are arranged on a linear polymer of deoxyribose phosphate. The four bases consist of thymine (T), adenine (A), cytosine (C), and guanine (G). The two strands of the DNA double helix are joined in accordance with well-known base pairing rules. These rules provide that thymine (T) joins with adenine (A) and that cytosine (C) joins with guanine (G). Accordingly, the base sequence along one strand determines the order of bases along the complementary strand.

Genetic information in DNA is known to be contained within the sequence of nucleotides in DNA strands. Heretofore, DNA sequencing has been accomplished by obtaining DNA from a source of interest and segregating a template DNA fragment. A complementary DNA fragment is synthesized by binding a primer ODN to the template fragment. This template fragment with the primer attached is then introduced into a solution containing deoxyribonucleoside triphosphates, DNA polymerase, buffer and magnesium ions.

Polymerase chain reaction testing, or PCR, is a process which utilizes a heat stable form of the DNA polymerase to extend the primer and transcribe the DNA template. The combination of template and primers is employed to limit the size of the DNA produced. This size can vary from a few dozen to several hundred or several thousand nucleotides in the DNA product. During the synthesis of this DNA product, certain labels are incorporated into the primer and/or the incoming nucleotides so that the product can be identified. The region of the genomic DNA that is transcribed is determined by the sequence of the primers employed. One primer is used in one strand of DNA and another is used for the complementary strand. The distance between the binding sites of the two primers determines the length of the DNA product. In one cycle of the polymerase chain reaction, the primer binds to the template DNA, the polymerase transcribes the template DNA beginning at the primer's 3' terminus and DNA products are released from the template. These events occur at different temperatures. Template binding occurs between 35°–50° C., polymerase activity between 60°–70° C., and the release between 85°–95° C. This cycle is repeated until sufficient DNA product is made to perform an analysis.

Recent advances in molecular biology and the schedule in the Human Genome Project have spurred the development of new methods for the labeling and detection of DNA and DNA fragments. Traditionally, radioisotopes have served as sensitive labels for DNA while, more recently, fluorescent, chemiluminescent and bioactive reporter groups have also been utilized. Fluorescent and chemiluminescent labels function by the emission of light as a result of the absorption of radiation and chemical reactions, respectively. Bioactive labels employ substances derived from living tissue.

The reporter group, $^{32}P$ or certain fluorescent or chemiluminescent substances, are usually incorporated in the primers or the deoxynucleoside triphosphates to label the newly synthesized DNA fragments. In the present application, the DNA fragments or ODN's are allowed to hybridize to a set of bound ODN's or DNA fragments that are immobilized on a solid surface. Because hybridization generally involves the formation of hydrogen bonds between A's and T's and between G's and C's in opposing DNA strands, the stable binding of one DNA to another through such hydrogen bonds reveals the sequence in the DNA fragments if the sequences of the immobilized ODNs are known. This process is sometimes referred to as "sequencing by hybridization" (SBH). The DNA on the solid surface is sometimes referred to as an "SBH chip" or a genosensor chip or a hybridization surface. This version of the SBH process is referred to as Format II SBH. E. Southern disclosed Format II SBH in International Application No. PCT/GB89/00460. Affymetrix, Inc. is very active in developing commercial products to perform Format II SBH.

Format I SBH is an alternative method where the genomic DNA is attached to a solid surface, such as a nylon membrane, and the ODNs of known sequence and containing labels are allowed to hybridize. R. Drmanac and R. Czerkvenjakov disclosed Format I SBH in U.S. Pat. No. 5,202,231, and are developing the analyses commercially at Hyseq Co.

While the above sequencing technique is capable of producing reliable results if properly applied, certain disadvantages are inherent in the process. For example, the ability to observe $^{32}P$ labels is limited by the length of the beta particle track produced by the disintegration of 32P. With fluorescent labels, the most common labels in use today, fluorescence from the solid surface of the SBH chip itself interferes with the detection of the signal from the fluorescent label on the DNA. It is common to see a signal to noise ratio of only 3:1 for fluorescent labels. Consequently, it is impracticable to employ a large number of labels simultaneously to extract many patterns of information from the SBH chip. In present practice, the simultaneous use of fluorescent labels in the emission spectrum is restricted to four labels. Similar restrictions and limitations are equally evident in experimentation which utilizes chemiluminescent labels.

Therefore, it is an object of this invention to provide a DNA sequencing process which uses stable or long-lived radioactive isotopes of various elements rather than short-lived lived radioactive isotopes or fluorescent or chemiluminescent labels.

Another object of this invention is to provide a process in which more than one DNA may be analyzed simultaneously.

A further object of this invention is to use mass spectrometric techniques for locating the stable or long-lived radioactive isotopic label(s) attached to the DNA fragments or the ODNS.

Additionally, it is an object of this invention to provide a process in which the attachment of stable or long-lived radioactive isotopes is compatible with the conditions employed for sequencing.

It is also an object of this invention to provide a process in which the presence of the stable or long-lived radioactive isotopes of various elements does not adversely affect the sequencing reactions or differentially alter the hybridization of the DNA fragments.

An additional object of this invention is to employ stable or long-lived radioactive isotopes to label DNAs that are used as probes in locating other DNAs that have been subjected to gel electrophoresis, such as in Southern blotting, or that have been placed on membranes or other surfaces, such as in dot blotting or direct blotting or genomic libraries.

Moreover, it is an object of this invention to provide a process which allows detection, significantly above background, of each of the specific isotopes of a given element in atomic or molecular form.

DISCLOSURE OF THE INVENTION

In accordance with various features of the present invention, a DNA sequencing process using stable or long-lived radioactive isotopes of various elements is provided. The process includes the step of incorporating one or more atoms of a specific stable or long-lived radioactive isotope of a selected element on the ODN primer or the DNA, or in one or more of the deoxynucleoside triphosphates such that a DNA fragment has a specific stable or long-lived radioactive isotope of a specified selected element at a terminal or interior position. The labeled DNA fragments are hybridized to stationary fragments on the hybridization surface or to DNAs that have been placed on membranes associated with genomic libraries or in the process of Southern blotting. The stable or long-lived radioactive isotopes are then analyzed using resonance ionization spectroscopy (RIS) techniques to determine the position they occupy on the hybridization surface.

Peptide nucleic acids (PNAs) are composed of monomers of 2-aminoethylglycine with nucleic acid bases A,G, C, or T attached to the individual monomers. These PNAs can replace the DNA fragments in the sequencing, mapping and diagnostic processes of this invention. The advantages of doing so are that the salt concentration can be decreased greatly during hybridization and that the bonding strength between a PNA and a DNA is greater than between two DNAS.

RIS is a laser based technique for ultra-trace element analysis whose concepts are incorporated herein by reference. The stable or long-lived radioactive isotopes are chosen such that specific labels are given for each primer selected for the PCR process.

There are a number of stable or long-lived radioactive isotopes that are useable and are detectable by RIS combined with mass spectroscopy. The specific stable or long-lived radioactive isotope is chemically incorporated on the primer or in the nucleotides that are incorporated by the DNA polymerase or into the ODNs used in Format I. In Format II, the labeled DNA fragments are synthesized and hybridized to a set of ODNs of known sequences that are fixed on a solid surface. In Format I, Southern blotting, dot blotting or genomic libraries, DNAs of unknown sequences are attached to a solid surface and labeled ODNs are hybridized to the fixed DNAS. The sequence of unknown DNA is known from the sequence of the DNAs or ODNs of known sequence to which it is hybridized.

Among the surfaces to which the DNAs are attached are glass, silicon oxide, gold surfaces, platinum surfaces, nylon membranes, Pyrex or polypropylene. It is also possible to employ a gold or platinum film over some solid support and attach the DNAs to that film using known chemistries which facilitate this objective.

The sequence is read by scanning the hybridization surface with RIS to detect a single isotope or with RIS coupled to a mass spectrometer to detect multiple isotopes. The identity of DNAs in Southern blotting is recognized by the labeled DNA that hybridizes to it. Use of a combination of elements having twenty stable or long-lived radioactive isotopes of unique mass allows twenty DNA samples to be identified simultaneously on a single chip by RIS coupled to a time-of-flight mass spectrometer. This is an example of multiplexing using Format II. Using Format I or Southern blotting or genomic libraries, thousands of DNAs are attached to a surface, typically a nylon membrane, and their sequences probed simultaneously with twenty different ODNs, each labeled with one of a set of twenty non-isobaric stable or long-lived radioactive isotopes.

Other mass spectrometric detection techniques such as secondary ion mass spectrometer (SIMS), laser microprobe mass analysis (LAMMA), and non-resonant or sub-nanosecond post-ionization techniques can also be used to detect the multiple isotopes in either atomic or molecular form. One or the other, including RIS, may be advantageous for specific applications for DNA analysis.

BEST MODE FOR CARRYING OUT THE INVENTION

Figure 1A:
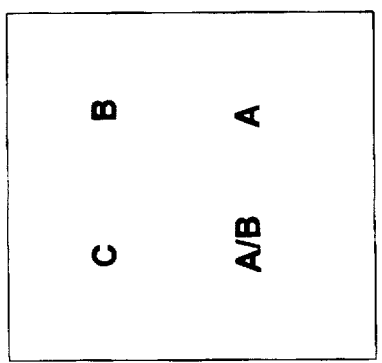
FIG. 1A illustrates an array design to prepare Form I SBH multiplexing samples. In this figure, A =M13mp18 DNA which contains a binding site for the $^{118}$Sn-M13(−20) ODN probe, and not for the $^{120}$Sn-T7 probe. "Target" is used to describe the DNA whose sequence is being sought. "Probe" is used to describe the oligonucleotide of known sequence. B=pSP70 DNA which has a binding site to the $^{120}$Sn-T7 probe and not for the $^{118}$Sn-M13(−20) probe. C=pBR322 DNA (which does not have binding sites for either probe).
Figure 1C:
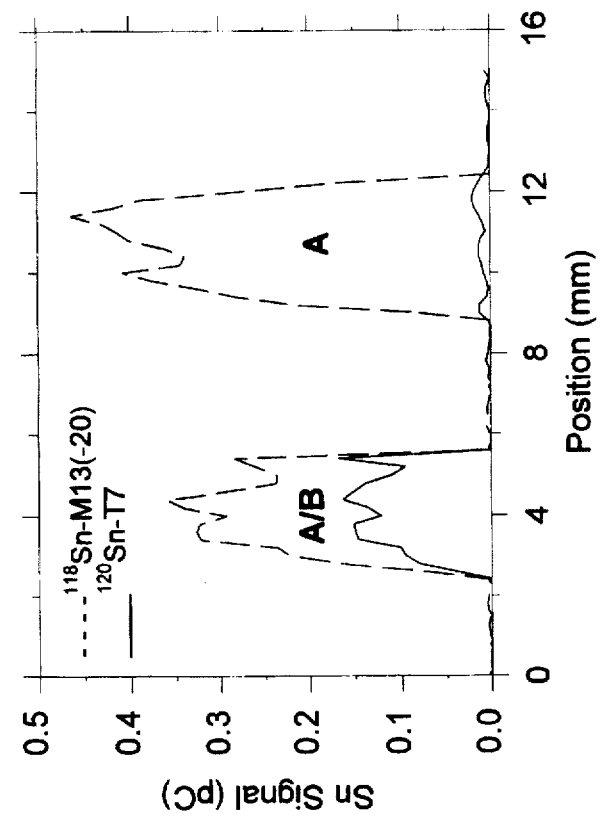
FIG. 1C demonstrates the results for the bottom half of the 4-dot array shown in FIG. 1A. The peaks on the left are $^{118}$Sn and $^{120}$Sn, corresponding to both the $^{118}$Sn M13(−20) and $^{120}$Sn-T7 probes. Both probes were expected to hybridize at this position because both M13mp18 DNA and pSP70 DNA were bound in this spot. The peak on the right represents $^{118}$Sn, corresponding to the $^{118}$Sn M13(−20) probe. M13mp18 DNA, which is complementary to the M13(−20) and not to the T7, was bound to the nylon in this position.
Figure 1B:
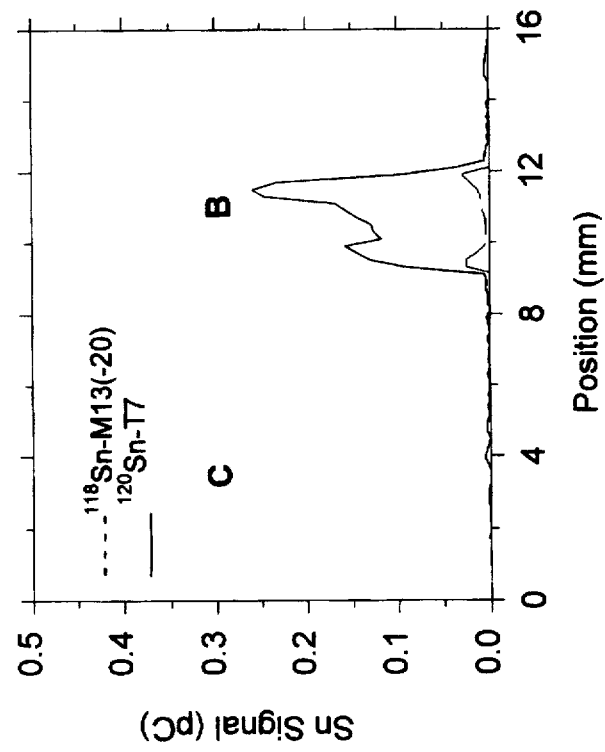
FIG. 1B shows the results for a Laser Atomization Resonance Ionization Spectroscopy (LARIS) line scan of the top half of the 4-dot array shown in FIG. 1A. Enriched tin is not detected on the left half of the scan at the position where pBR322 DNA is bound because pBR322 does not bind with either probe. The peak on the right corresponds to $^{120}$Sn. At this position, pSP70, which binds with the $^{120}$Sn-T7, is located.
Figure 2A:
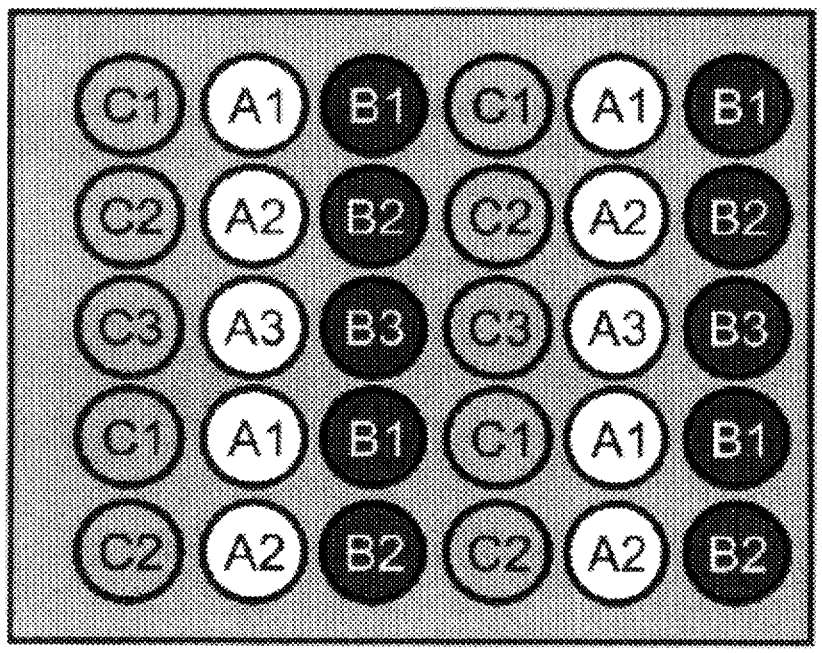
FIG. 2A illustrates a second array design used to prepare Form I SBH multiplexing samples. A=M13mp18 DNA which contains a binding site for the $^{118}$Sn-M13(−20) ODN probe and not for the $^{120}$Sn-T7 probe. B=pSP70 DNA which has a binding site to the $^{120}$Sn-T7 probe and not for the $^{118}$Sn-M13(−20) probe. C=pBR322 DNA (which does not have binding sites for either probe). The numbers after the letters refer to the concentrations of the solutions: 1=200 ng/µL for M13mp18 and 500 ng/µL for pBR322 and pSP70, 2=100 ng/µL and 3=20 ng/µL for all the DNAs.
Figure 2B:
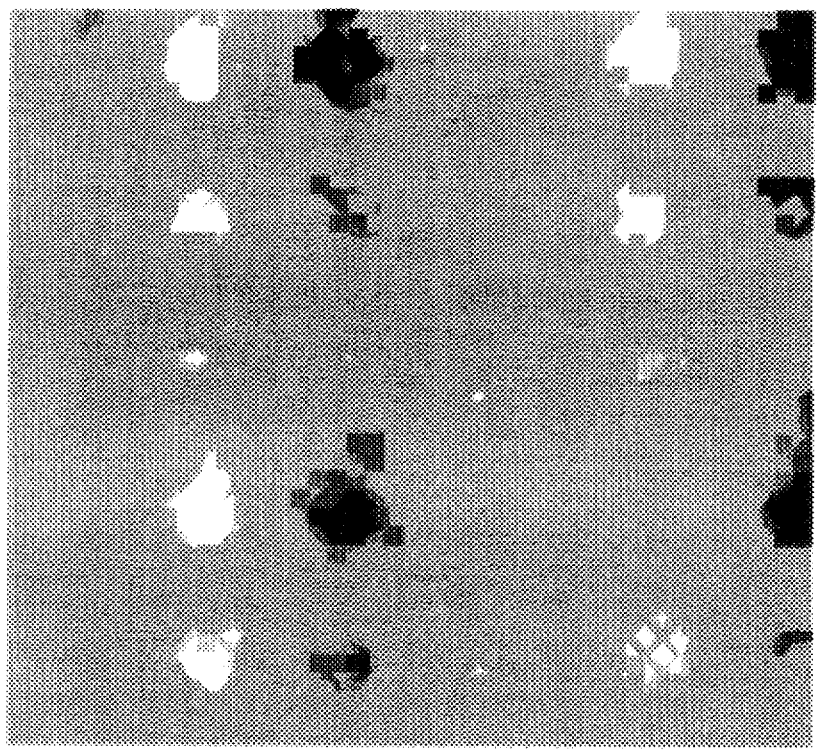
FIG. 2B shows a two-dimensional LARIS image of the Matrix described in FIG. 2A. The intensity scale is for the ratio $^{118}$Sn/$^{120}$Sn. The sample was hybridized with $^{118}$Sn-M13(−20) ODN and $^{120}$Sn-T7. At the positions where M13mp18 is bound, $^{118}$Sn is detected, and similarly, at the positions where pSP70 is bound, $^{120}$Sn-T7 is detected. One spot for the M13mp18, in the fourth row is missing and may not have been spotted. Enriched Sn is not detected where pBR322 DNA is located. The level of signal is dependent upon the amount of the DNA bound to the nylon.
Figures 3A, 3B:
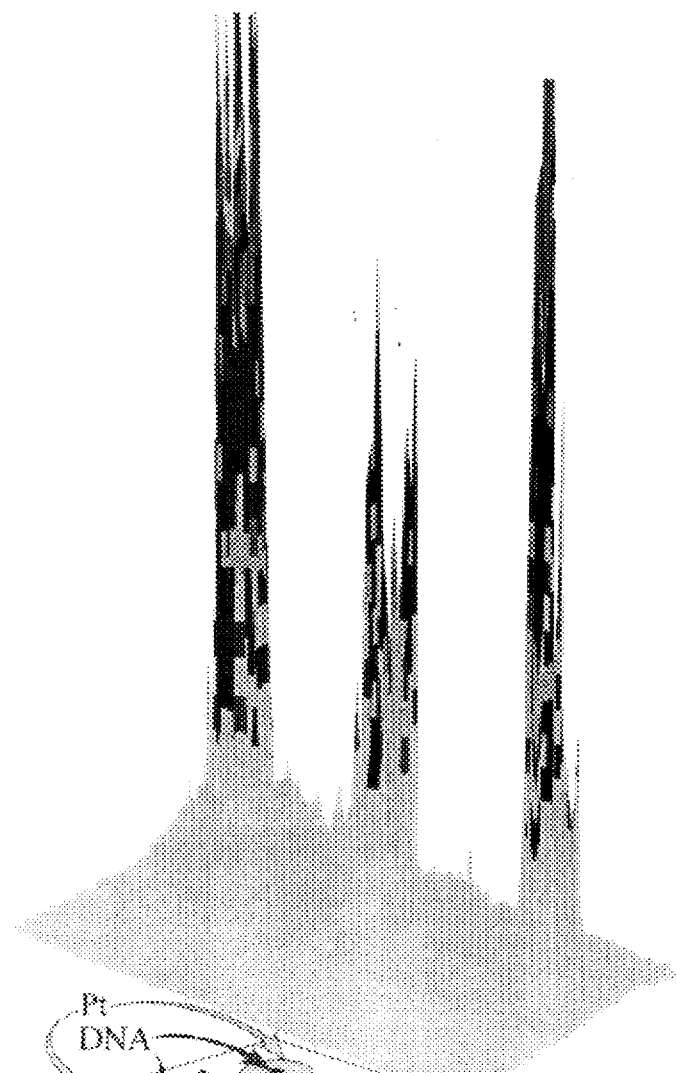
FIG. 3A illustrates an array design used to prepare Form II SBH multiplexing samples. The top and bottom rows of platinum circles were bound with two different 17-mer probe ODNs. The $^{118}$Sn-labeled target ODN shown below the flask was used to hybridize the sample and was completely complementary to the probe in the top row.
FIG. 3B shows a three-dimensional SIRIS image of the matrix described in FIG. 3A. At the positions where the complementary probe is bound, enriched $^{118}$Sn is detected, and similarly, at the positions where the non-complementary probe is bound, $^{118}$Sn in not detected. The middle spot displays a lower signal because this spot was analyzed with SIRIS several times before this image, removing some of the target ODN.

RIS analysis requires free atoms in the gas phase. This is achieved for the labeled DNA samples by bombarding the solid with a pulsed ion beam (sputter-initiated RIS or SIRIS) or with a pulsed laser beam (laser atomization RIS or LARIS) and creating an expanding cloud of neutral particles. The expanding cloud of particles is probed by the RIS laser(s) to cause excitation and then ionization of the selected element within the volume intersected by the laser beam(s). These ions are extracted into a mass spectrometer to separate and detect isotopes of the ionized element. With the use of a time-of-flight mass spectrometer, all isotopes of an element can be detected simultaneously. Using stable or long-lived radioactive isotopes from several elements, several RIS lasers are used to ionize the selected elements and isotopes simultaneously.

Stable or long-lived radioactive isotopes of metals are typically supplied as the metal or metal oxides and the synthesis of organometallic compounds has to involve reactions that begin with the metal in that form.

Synthesis of ODNs that are labeled with metals, such as 15–20 nucleotide primers, is performed by standard phosphoramidite chemistry and the 5′-terminus of each oligomer is derivatized with a primary alkyl amine group. The synthesis of the ODNs containing a primary amine group at the 5′-terminus is performed by a final round of synthesis with 5′-Amino Modifier C6 such as can be obtained from the Glen Research Corp. Following deprotection and purification of the $NH_2$-$(CH_2)_6$-oligonucleotide, the primary amine group is then reacted with TESPA NHS ester or DOTA isothiocyanate. The N-hydroxysuccinimide ester of triethylstannylpropionic acid (TESPA) is prepared from tin oxide and the resulting compound is then reacted with the amine group of the hexylamine modified ODN to form a product consisting of an ODN attached to the tin containing TESPA via an amine. The 1,4,7,10-tetraazacyclododecane-1,4,7,10-tetraacetic acid (DOTA) is synthesized with a nitrobenzyl group attached to one of the $CH_2$ groups. The nitro group is converted first to an amine and then to isothiocyanate. Reaction of the isothiocyanate with a hexylamine linker arm, attached to the 5′ position of an ODN, provides a method of labeling the DNA. The rare earth isotope can be added to the benzylisothiocyano-DOTA ligand, or the ligand can be reacted with the ODN after the addition of the rare earth ion.

Those skilled in the art will recognize that this method is not the only method of labeling DNA with a metal and is described as one example of an enabled means of labelling DNA with a metal and is not intended to limit the scope of the specification. Those skilled in the art will also recognize that pulsed beam lasers include high repetition rate femtosecond and sub-nanosecond lasers. Further, they will recognize that the above steps would be repeated to label a primer with tin that has been enriched with a different stable or long-lived radioactive isotope. Those skilled in the art will also recognize that the above-described process is also adaptable for the use of stable radioactive isotopes of other elements, including rare earths, that a practitioner may desire to use.

In accordance with the teachings of the present invention, a stable or long-lived radioactive isotope of a selected element is incorporated on the 5′-end of a primer ODN and/or in at least one of the dNTPs such that each new fragment type produced by PCR has a specific isotope associated with it. Moreover, the specific stable or long-lived radioactive isotope can be incorporated in an organic complex which in turn is incorporated into the primer. ODN or dNTP and used as the label or tag for the different ODNs or DNAs. Furthermore, it is possible to attach more than one atom of the stable or long-lived radioactive isotope to any DNA primer or dNTP so that the RIS could detect the DNA fragment more readily. Alternatively, it is possible to incorporate multiple atoms of a given stable or long-lived radioactive isotope into dendrimers which can be used to label DNA. Similarly, it is also possible to incorporate various isotopes of tin into DNA primers.

Using PCR, defined strands of the double stranded DNA are replicated using ODNs that are labeled with one or more atoms of a stable or long-lived radioactive isotope and/or by using deoxyribonucleotide triphosphates that have one or more atoms of a stable or long-lived radioactive isotope attached. Thus, the DNAs produced from these defined strands are labeled since the ODNs are included in the replicated strands. These labeled strands are then used for hybridization to a set of test DNAs in the SBH process or blotting method to determine the identity or the sequence of the DNA produced from the defined DNA strand. The tin, or other element, isotope serves as a discrete label that is associated with a specific DNA. In this manner, the replicated fragment is detected independently and simultaneously with other replicated fragments labeled with different stable or long lived radioactive isotopes.

Either SIRIS or LARIS may be employed to scan a SBH chip mounted on a support by moving the target position while the ion or laser beam position remains fixed. Alternatively, the sample can remain fixed in the position and the surface scanned with an ablating ion or laser beam. With SIRIS or LARIS, the sputtering beams can be focused to <10 μm in diameter to improve the resolution between adjacent DNA positions of the chip.

The speed of analysis made possible by SIRIS or LARIS surpasses any currently available art. As an example, when the SBH chip contains 1000 DNA test sites that are spaced 20 μm apart, the rate of scanning for stable or long-lived radioactive isotope-bound DNAs that have hybridized to any of the sites may be calculated. It is commonly known that copper vapor-pumped dye lasers fire at the rate of 6000 shots per second or higher. If three shots are taken at each DNA site, then 1000 sites are analyzed in 0.5 second. Allowing 0.5 second to move from one site to another on the SBH chip adds 500 seconds to the time required to scan the entire set of 1000. If eight isotopes are used simultaneously then eight patterns can be determined in the same amount of time. The use of twenty specific stable or long-lived radioactive isotopes allows the simultaneous determination of SBH patterns and sequence information from twenty DNAs simultaneously.

Those skilled in the art will readily recognize that the present invention could also be practiced for determining RNA sequences. One skilled in the art could obtain DNA by reverse transcription of RNA from the source of interest.

Data from the RIS analysis can be displayed digitally or in graphic form that is comparable to images obtained from autoradiography or fluorescent analyses. The sequence obtained could be printed out directly and any uncertainties designated. More complex multiplexing can be accomplished with stable or long-lived radioactive isotopes than with fluorescent labels since the latter can use only about four labels at a time whereas the stable or long-lived radioactive isotope labels can be used as many as twenty or more to a set. Relative to radiation safety, the purchase and disposal of radioisotopes is eliminated and the process is safer for personnel.

From the foregoing description, it will be recognized by those skilled in the art that the present DNA sequencing, mapping, and diagnostic processes, which utilize hybridization and stable or long-lived isotope labels of DNA or ODNs, genomic library membranes or Southern blotting membranes, offer several distinct advantages over the prior art. Specifically, the DNA Sequencing, Mapping, and Diagnostic Processes Using Hybridization and Stable Isotope Labels of DNA provide a process for attaching stable or long-lived radioactive isotopes to DNA fragments from sources of interest. They provide greater longevity than the radioactive substances used to label and identify the newly synthesized DNA fragments. The Sequencing, Mapping, and Diagnostic Processes eliminate fluorescence and interference in signal detection which results when reading a fluorescent label on DNA fixed to a SBH chip. Moreover, these Processes facilitate the employment of a large number of labels to simultaneously extract many patterns of information from the SBH chip.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention,

We claim:

1. A DNA sequencing, mapping, and diagnostic process using known individual isotopes, including stable isotopes and long-lived radioactive isotopes, associated with individual oligodeoxynucleotides (ODNs) or peptide nucleic acids (PNAs), said process comprising the steps of:

labeling nucleotide segments or PNAs with said known isotopes of an element that does not normally occur in DNAs or ODNs;

causing said labeled, complementary, free nucleotide segments or PNAs to hybridize to fixed nucleotide segments or PNAs, said fixed nucleotide segments or PNAs being immobilized in distinct positions on a hybridization surface in an array such that said nucleotide segments or PNAs with known sequences define sequences of nucleotide segments or PNAs that become hybridized;

rinsing non-hybridized labeled nucleotide segments or PNAs from said hybridization array; and using mass spectrometric methods to analyze the presence and position on said array of said hybridized, labeled complementary nucleotide segments or PNAs and identifying said isotopes.

2. The DNA sequencing, mapping, and diagnostic process of claim 1 wherein said labeled nucleotide segments are oligodeoxynucleotides (ODNs) and said fixed nucleotide segments are DNAs.

3. The DNA sequencing, mapping, and diagnostic process of claim 1 wherein said labeled nucleotide segments are DNAs and said fixed nucleotide segments are oligodeoxynucleotides (ODNs).

4. The DNA sequencing, mapping, and diagnostic process of claim 1 wherein said labeled nucleotide segments or peptide nucleic acids (PNAs) are DNAs and said fixed nucleotide segments or PNAs are PNAs.

5. The DNA sequencing, mapping, and diagnostic process of claim 1 wherein said labeled nucleotide segments or peptide nucleic acids (PNAs) are PNAs and said fixed nucleotide segments or PNAs are DNAs.

6. The DNA sequencing, mapping, and diagnostic process of claim 1 wherein said hybridization array surface is composed of an appropriate available chemical material, said material including those selected from the group consisting of glass, Pyrex, silicon oxide, nylon membranes, polypropylene, gold surfaces and platinum surfaces.

7. The DNA sequencing, mapping, and diagnostic process of claim 6 wherein a plurality of said known isotopes are used to individually label several nucleotide segments so that data is multiplexed.

8. The DNA sequencing, mapping, and diagnostic process of claim 7 wherein said isotopes used to label said nucleotide segments are enriched several-fold over natural abundance to make them easily detectable and allow many non-isobaric isotopes to be used simultaneously to provide a multiplex type of analysis.

9. The DNA sequencing, mapping, and diagnostic process of claim 8 wherein said hybridization array surface is used to detect mutations in DNA by designing said nucleotide segments to contain sequences that would distinguish normal from abnormal DNA sequences of the gene in question.

10. The DNA sequencing, mapping, and diagnostic process of claim 8 wherein said hybridization surface is designed to provide an error check for raw DNA sequence data obtained by other techniques such as gel electrophoresis.

11. The DNA sequencing, mapping, and diagnostic process of claim 1 wherein said mass spectrometric methods used to detect the presence of said labeled, complementary hybridized nucleotide segments on said hybridization array surface include at least one method selected from the group consisting of time-of-flight, quadrupole, magnetic sector and ion trap mass spectrometry.

12. The DNA sequencing, mapping, and diagnostic process of claim 1 wherein said labeled, complementary hybridized nucleotide segments detected on said hybridization array surface are analyzed by surface analysis techniques which require vaporization or those techniques which do not require vaporization.

13. The DNA sequencing, mapping, and diagnostic process of claim 12 wherein said labeled, complementary hybridized nucleotide segments are vaporized and then analyzed by techniques which require ionization or those techniques not requiring ionization.

14. The DNA sequencing, mapping, and diagnostic process of claim 13 wherein said labeled, complementary hybridized nucleotide segments are vaporized and then analyzed using non-ionization techniques selected from the group of methods consisting of resonant and non-resonant Raman spectroscopy, absorption spectroscopy, and optical emission of laser ablated material and ion beam sputtered material.

15. The DNA sequencing, mapping, and diagnostic process of claim 13 wherein said labeled, complementary hybridized nucleotide segments disposed on said hybridization surface are vaporized and analyzed using resonant and non-resonant ionization methods.

16. The DNA sequencing, mapping, and diagnostic process of claim 15 wherein said vaporization of said labeled, complementary hybridized nucleotide segments which are vaporized and then analyzed using resonance ionization method is performed by techniques selected from the group consisting of ion beam sputtering, sputter-initiated resonance ionization spectroscopy (SIRIS), laser ablation, laser-induced desorption, laser atomization resonance ionization spectroscopy (LARIS) and thermal techniques.

17. The DNA sequencing, mapping, and diagnostic process of claim 16 wherein said lasers used in performance of said resonance ionization are wavelength tunable lasers pumped by lasers selected from the group consisting of continuous wave lasers and pulsed lasers.

18. The DNA sequencing, mapping, and diagnostic process of claim 17 wherein said wavelength tunable lasers are selected from the group consisting of dye, solid-state, and optical parametric oscillator lasers.

19. The DNA sequencing, mapping, and diagnostic process of claim 17 wherein said pulsed lasers are selected from the group consisting of excimer, neodymium ion doped yttrium aluminum garnet crystal (Nd:YAG) Cu-vapor, and sub-nanosecond lasers.

20. The DNA sequencing, mapping, and diagnostic process of claim 15 wherein said vaporization of said labeled, complementary hybridized nucleotide segments which are vaporized and then analyzed using non-resonant ionization is performed by techniques selected from the group consisting of ion beam sputtering, laser ablation, laser-induced desorption, and thermal techniques.

21. The DNA sequencing, mapping, and diagnostic process of claim 20 wherein said non-resonant ionization is performed using a method selected from the group consisting of continuous wave lasers, pulsed lasers and electrons.

22. The DNA sequencing, mapping, and diagnostic process of claim 21 wherein said pulsed lasers are selected from the group consisting of excimer, neodymium ion doped yttrium aluminum garnet crystal (Nd:YAG), Cu-vapor, and sub-nanosecond lasers.

23. The DNA sequencing, mapping, and diagnostic process of claim 12 wherein said labeled, complementary hybridized nucleotide segments which are analyzed by techniques not requiring vaporization are analyzed by methods requiring ionization or those methods not requiring ionization.

24. The DNA sequencing, mapping, and diagnostic process of claim 23 wherein said labeled, complementary hybridized nucleotide segments which are non-vaporized are analyzed by performance of surface analysis methods not requiring ionization selected from the group consisting of surface-enhanced Raman spectroscopy (SERS), second-harmonic generation (SHG), Auger electron spectroscopy and x-ray photon spectroscopy.

25. The DNA sequencing, mapping, and diagnostic process of claim 12 wherein said labeled, complementary hybridized nucleotide segments are vaporized and then analyzed by performance of methods selected from the group consisting of secondary ion mass spectroscopy (SIMS), laser ionization mass spectroscopy (LIMS), and laser microprobe mass analysis (LAMMA).

26. A DNA sequencing, mapping, and diagnostic process using known individual isotopes, including stable isotopes and long-lived radioactive isotopes, associated with individual oligodeoxynucleotides (ODNs), said process comprising the steps of:

labeling nucleotide segments with said known isotopes of an element that does not normally occur in DNAs or ODNs, said labeling nucleotides segments being one of said DNAs and said ODNs;

causing said labeled, complementary, free nucleotide segments to hybridize to fixed nucleotide segments, said fixed nucleotide segment being the other of said DNAs and said ODNs, said fixed nucleotide segments being immobilized in distinct positions on a hybridization surface in an array such that said nucleotide segments of said DNAs and said ODNs with known sequences define sequences of nucleotide segments that become hybridized;

rinsing non-hybridized labeled nucleotide segments from said hybridization array; and using mass spectrometric methods to analyze the presence and position on said array of said hybridized, labeled complementary nucleotide segments or ODNs and identifying said isotopes.

27. The DNA sequencing, mapping, and diagnostic process of claim 26 wherein said hybridization array surface is composed of an appropriate available chemical material, said material including those selected from the group consisting of glass, Pyrex, silicon oxide, nylon membranes, polypropylene, gold surfaces and platinum surfaces.

28. The DNA sequencing, mapping, and diagnostic process of claim 27 wherein a plurality of said known isotopes are used to individually label several nucleotide segments so that data is multiplexed.

29. The DNA sequencing, mapping, and diagnostic process of claim 28 wherein said isotopes used to label said nucleotide segments are enriched several-fold over natural abundance to make them easily detectable and allow many non-isobaric isotopes to be used simultaneously to provide a multiplex type of analysis.

30. The DNA sequencing, mapping, and diagnostic process of claim 29 wherein said hybridization array surface is used to detect mutations in DNA by designing said nucleotide segments to contain sequences that would distinguish normal from abnormal DNA sequences of the gene in question.

31. The DNA sequencing, mapping, and diagnostic process of claim 29 wherein said hybridization array surface is designed to provide an error check for raw DNA sequence data obtained by other techniques such as gel electrophoresis.

32. The DNA sequencing, mapping, and diagnostic process of claim 26 wherein said mass spectrometric methods used to detect the presence of said labeled, complementary hybridized nucleotide segments on said hybridization array surface include at least one method selected from the group consisting of time-of-flight, quadrupole, magnetic sector and ion trap mass spectrometry.

33. The DNA sequencing, mapping, and diagnostic process of claim 26 wherein said labeled, complementary hybridized nucleotide segments detected on said hybridization array surface are analyzed by surface analysis techniques which require vaporization or those techniques which do not require vaporization.

34. The DNA sequencing, mapping, and diagnostic process of claim 33 wherein said labeled, complementary hybridized nucleotide segments are vaporized and then analyzed by techniques which require ionization or those techniques not requiring ionization.

35. The DNA sequencing, mapping, and diagnostic process of claim 34 wherein said labeled hybridized nucleotide segments which are vaporized are analyzed using non-ionization techniques selected from the group of methods consisting of resonant and non-resonant Raman spectroscopy, absorption spectroscopy, and optical emission of laser ablated or ion beam sputtered material.

36. The DNA sequencing, mapping, and diagnostic process of claim 34 wherein said labeled, complementary hybridized nucleotide segments disposed on said hybridization surface are vaporized and then analyzed using resonant and non-resonant ionization methods.

37. The DNA sequencing, mapping, and diagnostic process of claim 36 wherein said vaporization of said labeled, complementary hybridized nucleotide segments which are vaporized and then analyzed using resonance ionization method is performed by techniques selected from the group consisting of ion beam sputtering, sputter-initiated resonance ionization spectroscopy (SIRIS), laser ablation, laser-induced desorption, laser atomization resonance ionization spectroscopy (LARIS) and thermal techniques.

38. The DNA sequencing, mapping, and diagnostic process of claim 37 wherein said lasers used in performance of said resonance ionization are wavelength tunable lasers pumped by lasers selected from the group consisting of continuous wave lasers and pulsed lasers.

39. The DNA sequencing, mapping, and diagnostic process of claim 38 wherein said wavelength tunable lasers are selected from the group consisting of dye, solid-state and optical parametric oscillator lasers.

40. The DNA sequencing, mapping, and diagnostic process of claim 38 wherein said pulsed lasers are selected from the group consisting of excimer, neodymium ion doped yttrium aluminum garnet crystal (Nd:YAG), Cu-vapor, and sub-nanosecond lasers.

41. The DNA sequencing, mapping, and diagnostic process of claim 36 wherein said vaporization of said labeled, complementary hybridized nucleotide segments which are vaporized and then analyzed using non-resonant ionization is performed by techniques selected from the group consisting of ion beam sputtering, laser ablation, laser-induced desorption, and thermal techniques.

42. The DNA sequencing, mapping, and diagnostic process of claim 41 wherein said lasers used in performance of said non-resonant ionization are selected from the group consisting of continuous wave and pulsed lasers.

43. The DNA sequencing, mapping, and diagnostic process of claim 42 wherein said pulsed lasers are selected from the group consisting of excimer, neodymium ion doped yttrium aluminum garnet crystal (Nd:YAG), Cu-vapor, and sub-nanosecond lasers.

44. The DNA sequencing, mapping, and diagnostic process of claim 33 wherein said labeled, complementary hybridized nucleotide segments which are analyzed by techniques not requiring vaporization are analyzed by methods requiring ionization or those methods not requiring ionization.

45. The DNA sequencing, mapping, and diagnostic process of claim 44 wherein said labeled, complementary hybridized nucleotide segments which are non-vaporized are analyzed by performance of surface analysis methods not requiring ionization selected from the group consisting of surface-enhanced Raman spectroscopy (SERS), second-harmonic generation (SHG), Auger electron spectroscopy and x-ray photon spectroscopy.

46. The DNA sequencing, mapping, and diagnostic process of claim 33 wherein said labeled, complementary hybridized nucleotide segments are vaporized and than analyzed by performance of methods selected from the group consisting of secondary ion mass spectroscopy (SIMS), laser ionization mass spectroscopy (LIMS), and laser microprobe mass analysis (LAMMA).

47. A DNA sequencing, mapping, and diagnostic process using known individual isotopes, including stable isotopes and long-lived radioactive isotopes, associated with individual oligodeoxynucleotides (ODNs) or peptide nucleic acids (PNAs), said process comprising the steps of:
  labeling nucleotide segments of PNAs with said known isotopes of an element that does not normally occur in DNAs or PNAs, said labeling nucleotide segments or PNAs being one of said PNAs and said DNAs;
  causing said labeled, complementary, free nucleotide segments or PNAs to hybridize to fixed nucleotide segments or PNAs, one of said fixed or free nucleotide segments or PNAs being PNAs, said fixed nucleotide segments or PNAs being immobilized in distinct positions on a hybridization surface in an array such that said PNAs with known sequences define sequences of nucleotide segments that become hybridized;
  rinsing non-hybridized labeled nucleotide segments or PNAs from said hybridization array; and
  using mass spectrometric methods to analyze the presence and position on said array of said hybridized, labeled complementary nucleotide segments or PNAs and identifying said isotopes.

48. The DNA sequencing, mapping, and diagnostic process of claim 47 wherein said hybridization array surface is composed of an appropriate available chemical material, said material including those selected from the group consisting of glass, Pyrex, silicon oxide, nylon membranes, polypropylene, gold surfaces and platinum surfaces.

49. The DNA sequencing, mapping, and diagnostic process of claim 48 wherein a plurality of said known isotopes are used to individually label several nucleotide segments or PNAs so that data is multiplexed.

50. The DNA sequencing, mapping, and diagnostic process of claim 49 wherein said isotopes used to label said nucleotide segments or PNAs are enriched several-fold over natural abundance to make them easily detectable and allow many non-isobaric isotopes to be used simultaneously to provide a multiplex type of analysis.

51. The DNA sequencing, mapping, and diagnostic process of claim 50 wherein said hybridization array surface is used to detect mutations in DNA by designing said nucleotide segments or PNAs to contain sequences that would distinguish normal from abnormal DNA sequences of the gene in question.

52. The DNA sequencing, mapping, and diagnostic process of claim 50 wherein said hybridization surface is designed to provide an error check for raw DNA sequence data obtained by other techniques such as gel electrophoresis.

53. The DNA sequencing, mapping, and diagnostic process of claim 47 wherein said mass spectrometric methods used to detect the presence of said labeled, complementary hybridized nucleotide segments or PNAs on said hybridization array surface include at least one method selected from the group consisting of time-of-flight, quadrupole, magnetic sector and ion trap mass spectrometry.

54. The DNA sequencing, mapping, and diagnostic process of claim 47 wherein said labeled, complementary hybridized nucleotide segments or PNAs detected on said hybridization array surface are analyzed by surface analysis techniques which require vaporization or those techniques which do not require vaporization.

55. The DNA sequencing, mapping, and diagnostic process of claim 54 wherein said labeled, complementary hybridized nucleotide segments or PNAs are vaporized and then analyzed by techniques which require ionization or those techniques not requiring ionization.

56. The DNA sequencing, mapping, and diagnostic process of claim 55 wherein said labeled hybridized nucleotide segments or PNAs which are vaporized are analyzed using non-ionization techniques selected from the group of methods consisting of resonant and nonresonant Raman spectroscopy, absorption spectroscopy, and optical emission of laser ablated or ion beam sputtered material.

57. The DNA sequencing, mapping, and diagnostic process of claim 55 wherein said labeled, complementary hybridized nucleotide segments or PNAs disposed on said hybridization surface are vaporized and then analyzed using resonant and non-resonant ionization methods.

58. The DNA sequencing, mapping, and diagnostic process of claim 57 wherein said vaporization of said labeled, complementary, hybridized nucleotide segments or PNAs which are vaporized and then analyzed using resonance ionization method is performed by techniques selected from the group consisting of ion beam sputtering, sputter-initiated resonance ionization spectroscopy (SIRIS), laser ablation, laser-induced desorption, laser atomization resonance ionization spectroscopy (LARIS) and thermal techniques.

59. The DNA sequencing, mapping, and diagnostic process of claim 58 wherein said lasers used in performance of said resonance ionization are wavelength tunable lasers pumped by lasers selected from the group consisting of continuous wave lasers and pulsed lasers.

60. The DNA sequencing, mapping, and diagnostic process of claim 59 wherein said wavelength tunable lasers are selected from the group consisting of dye, solid-state and optical parametric oscillator lasers.

61. The DNA sequencing, mapping, and diagnostic process of claim 59 wherein said pulsed lasers are selected from the group consisting of excimer, neodymium ion doped yttrium aluminum garnet crystal (Nd:YAG), Cu-vapor, and sub-nanosecond lasers.

62. The DNA sequencing, mapping, and diagnostic process of claim 57 wherein said vaporization of said labeled, complementary, hybridized nucleotide segments or PNAs which are vaporized and then analyzed using non-resonant ionization is performed by techniques selected from the group consisting of ion beam sputtering, laser ablation, laser-induced desorption and thermal techniques.

63. The DNA sequencing, mapping, and diagnostic process of claim 62 wherein said non-resonant ionization is performed using a method selected from the group consisting of continuous wave lasers, pulsed lasers and electrons.

64. The DNA sequencing, mapping, and diagnostic process of claim 63 wherein said pulsed lasers are selected from the group consisting of excimer, neodymium ion doped yttrium aluminum garnet crystal (Nd:YAG), Cu-vapor, and sub-nanosecond lasers.

65. The DNA sequencing, mapping, and diagnostic process of claim 54 wherein said labeled, complementary, hybridized nucleotide segments or PNAs which are analyzed by techniques not requiring vaporization are analyzed by methods requiring ionization or those methods not requiring ionization.

66. The DNA sequencing, mapping and diagnostic process of claim 65 wherein said labeled, complementary, hybridized nucleotide segments or PNAs which are non-vaporized are analyzed by performance of surface analysis methods not requiring ionization selected from the group consisting of surface-enhanced Raman spectroscopy (SERS), second-harmonic generation (SHG), Auger electron spectroscopy and x-ray photon spectroscopy.

67. The DNA sequencing, mapping, and diagnostic process of claim 54 wherein said labeled, complementary, hybridized nucleotide segments or PNAs are vaporized and then analyzed by performance of methods selected from the group consisting of secondary ion mass spectroscopy (SIMS), laser ionization mass spectroscopy (LIMS), and laser microprobe mass analysis (LAMMA).

* * * * *